(12) United States Patent
Shiotani et al.

(10) Patent No.: US 9,428,429 B2
(45) Date of Patent: Aug. 30, 2016

(54) METHOD FOR PRODUCING FLUORINE-CONTAINING ALKANE

(75) Inventors: Yuko Shiotani, Settsu (JP); Kakeru Hanabusa, Settsu (JP); Takehiro Chaki, Settsu (JP); Kazuhiro Takahashi, Settsu (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 13/634,047

(22) PCT Filed: Feb. 18, 2011

(86) PCT No.: PCT/JP2011/053551
§ 371 (c)(1),
(2), (4) Date: Sep. 11, 2012

(87) PCT Pub. No.: WO2011/122157
PCT Pub. Date: Oct. 6, 2011

(65) Prior Publication Data
US 2013/0006022 A1    Jan. 3, 2013

(30) Foreign Application Priority Data

Mar. 31, 2010 (JP) ................................. 2010-080914
Feb. 15, 2011 (JP) ................................. 2011-029637

(51) Int. Cl.
*C07C 17/354* (2006.01)
*C07C 17/23* (2006.01)

(52) U.S. Cl.
CPC .............. *C07C 17/23* (2013.01); *C07C 17/354* (2013.01)

(58) Field of Classification Search
CPC .................................................. C07C 17/354
USPC ....................................................... 570/175
See application file for complete search history.

(56) References Cited

U.S. PATENT DOCUMENTS

2007/0123741 A1*  5/2007  Van Der Puy et al. ........ 570/123

FOREIGN PATENT DOCUMENTS

| JP | 8-119885 | 5/1996 |
| JP | 8-119886 | 5/1996 |
| JP | 8-165256 | 6/1996 |
| JP | 2001-240569 | 9/2001 |
| JP | 2001240569 A * | 9/2001 |
| JP | 2008-162999 | 7/2008 |
| WO | WO 2008054778 A2 * | 5/2008 |

OTHER PUBLICATIONS

Kin, Y. N. et al. JP2001240569A (English translation).*
Kin et al. JP2001240569A (English translation).*
International Search Report issued May 17, 2011 in International (PCT) Application No. PCT/JP2011/053551.
I. L. L Knunyants et al., "Reactions of Fluoro Olefins", Otdelenie Khimicheskikh Nauk, No. 8, pp. 1412-1418, Aug. 1960 (with English translation).

* cited by examiner

*Primary Examiner* — Fereydoun G Sajjadi
*Assistant Examiner* — Medhanit Bahta
(74) *Attorney, Agent, or Firm* — Wenderoth, Lind & Ponack, L.L.P.

(57) ABSTRACT

The present invention provides a method for producing a fluorine-containing alkane, which comprises reacting at least one fluorine-containing compound selected from the group consisting of chlorine-containing fluoroalkanes and fluorine-containing alkenes with hydrogen gas in the presence of catalysts, wherein two or more catalysts having different catalytic activities are used, and the fluorine-containing compound and hydrogen gas, which are starting materials, are sequentially brought into contact with the catalysts in the order of the catalyst having a lower catalytic activity followed by the catalyst having a higher catalytic activity. According to the present invention, in the method for producing a fluorine-containing alkane by using chlorine-containing fluoroalkane or fluorine-containing alkene as a starting material, and subjection it to a reduction reaction or a hydrogen addition reaction, the objective fluorine-containing alkane can be produced with high productivity.

4 Claims, No Drawings

METHOD FOR PRODUCING FLUORINE-CONTAINING ALKANE

This application is a U.S. national stage of International Application No. PCT/JP2011/053551 filed Feb. 18, 2011.

TECHNICAL FIELD

The present invention relates to a method for producing fluorine-containing alkane.

BACKGROUND ART

Fluorine-containing alkane is useful for various kinds of applications, such as a reaction intermediate, foaming agent, coolant and the like.

As an example of a known method for producing fluorine-containing alkane, fluorine-containing olefin is reduced at room temperature using a palladium catalyst (see Non Patent Literature 1 below). Another method is also reported wherein $CF_3CF=CF_2$ is reduced by hydrogen through a liquid phase reaction using $BaSO_4$, a palladium catalyst supported on activated carbon, etc. (see Patent Literature 1 below).

However, in order to achieve a high selectivity of the target fluorine-containing alkane in these methods, the reaction rate needs to be slowed down; therefore, it is impossible to produce fluorine-containing olefin efficiently on an industrial scale.

Patent Literature 2 below discloses a method for producing fluorinated propane, through a multistep reaction, using fluorine-containing olefin as a starting material by reacting it with hydrogen or a like reducing agent in the presence of a catalyst. A preferable embodiment of this method is such that the reaction is suppressed using only a small amount of catalyst at the initial stage of reaction and then the amount of the catalyst is gradually increased. It is said that this method achieves a high conversion rate and selectivity at a relatively high production speed.

However, in the method disclosed in Patent Literature 2, the amount of heat generated by the reaction becomes unduly large; therefore, removal of heat is necessary by a method, for example, that employs a reactor equipped with a jacket and removes heat using a refrigerant, or other means for cooling the reaction mixture, such as the use of an internal cooling coil, introduction of a diluent into the reaction mixture for additional cooling, and the like. This makes the structure of the reaction apparatus complicated. Furthermore, in order to avoid an excessive temperature rise, control of the introduction speed of the starting material compound becomes necessary, and this entails a reduction in the production efficiency of the target fluorine-containing alkane.

CITATION LIST

Patent Literature

PTL 1: Japanese Unexamined Patent Publication No. 1996-165256

PTL 2: Japanese Unexamined Patent Publication No. 2008-162999

Non Patent Literature

NPL 1: Izvest. Akad. Nauk S. S. S. R., Otdel. Khim. Nauk. (1960), 1412

SUMMARY OF INVENTION

Technical Problem

The present invention has been accomplished in view of the foregoing problems found in the prior art. A main object of the present invention is to provide a method for producing fluorine-containing alkane with high production efficiency in the method of using chlorine-containing fluoroalkane or fluorine-containing alkene as a starting material, and reacting it with hydrogen gas.

Solution to Problem

The present inventors conducted extensive research to achieve the above-described object. As a result, they found the following. When chlorine-containing fluoroalkane or fluorine-containing alkene is reacted with hydrogen gas to conduct a hydrogen addition reaction or a reduction reaction by hydrogen, the temperature rise during the reaction can be suppressed without reducing the conversion rate or selectivity by using a plurality of catalysts having different catalytic activities in such a manner that the first stage of the reaction is conducted under the presence of the catalyst having the lowest activity followed by multistep reactions using catalysts having sequentially higher catalytic activity in each step. As a result, the speed of introducing the starting materials can be increased and the production efficiency can be greatly improved. The present invention has been accomplished on the basis of this finding.

Specifically, the present invention provides the following method for producing fluorine-containing alkane.

Item 1. A method for producing fluorine-containing alkane comprising reacting at least one fluorine-containing compound selected from the group consisting of chlorine-containing fluoroalkanes and fluorine-containing alkenes with hydrogen gas in the presence of a catalyst, wherein two or more types of catalysts having different catalytic activities are used, and said at least one fluorine-containing compound and hydrogen gas, which are starting materials, are sequentially contacted with the catalysts in the order of lower to higher catalytic activity.

Item 2. The method according to Item 1, which uses a reaction apparatus in which two or more reaction tubes charged with catalysts having different catalytic activities are connected in series.

Item 3. The method according to Item 1 or 2, wherein each catalyst is one containing a noble metal component supported on a carrier.

Item 4. The method according to any one of Items 1 to 3, wherein the noble metal is at least one member selected from the group consisting of Pd, Pt, Ru and Rh, and the carrier is at least one member selected from the group consisting of activated carbon, porous alumina silicate, aluminum oxide, silicon oxide, titanium oxide, zirconium oxide, zinc oxide and aluminum fluoride.

Item 5. The method according to Item 3 or 4, wherein the catalysts having different catalytic activities are those containing identical noble metal components supported on identical carriers with different supporting amounts, and the fluorine-containing compound and hydrogen gas, which are starting materials, are sequentially contacted with a catalyst containing a smaller amount of noble metal component to a catalyst containing a larger amount of noble metal component.

Item 6. The method according to any one of Items 1 to 5, wherein the chlorine-containing fluoroalkane is at least one member selected from the group consisting of:

a compound represented by Formula (1):

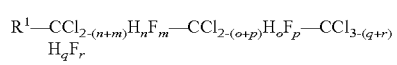

wherein $R^1$ is a alkyl group, a hydrogen atom, a fluorine atom, or a $C_{1-4}$ fluoroalkyl group that may contain a chlorine atom(s); n, m, o and p are each individually an integer of 0 to 2; q and r are each individually an integer of 0 to 3, with the proviso that n+m≤2, o+p≤2, q+r≤3, and n+m+o+p+q+r≤6; provided that when $R^1$ is neither a fluoroalkyl group nor a fluorine atom, the sum of m, p and r is 1 or greater; and a compound represented by Formula (2):

$$CCl_{3-(a+b)}H_aF_b\text{—}CCl_{3-(c+d)}H_cF_d$$

wherein a, b, c and d are each individually an integer of 0 to 3, a+b≤3, c+d≤3, b+d≥1, and a+b+c+d≤5; and the fluorine-containing alkene is a fluorine-containing alkene represented by Formula (3):

$$R^3Y^1C\text{=}CY^2R^4$$

wherein $R^3$ and $R^4$ may be the same or different and each represents a $C_{1-4}$ alkyl group, a hydrogen atom, a fluorine atom, a chlorine atom, or a $C_{1-4}$ fluoroalkyl group that may contain a chlorine atom(s); $Y^1$ and $Y^2$ may be the same or different and each represents a hydrogen atom, a fluorine atom or a chlorine atom; with the proviso that when $R^3$ and $R^4$ are neither a fluoroalkyl group nor a fluorine atom, at least one of $Y^1$ and $Y^2$ is a fluorine atom.

Item 7. The method according to any one of Items 1 to 6, wherein the chlorine-containing fluoroalkane is a compound represented by Formula (1-1): $R^2\text{—}CCl_{2-(j+k)}H_jF_k\text{—}CCl_{3-(l+t)}H_lF_t$ wherein $R^2$ is a $C_{1-3}$ alkyl group, a hydrogen atom, a fluorine atom, or a $C_{1-3}$ fluoroalkyl group that may contain a chlorine atom(s); j and k are each individually an integer of 0 to 2; l and t are each individually an integer of 0 to 3; j+k≤2; l+t≤3; and j+k+l+t≤4; with the proviso that when $R^2$ is neither a fluoroalkyl group nor a fluorine atom, the sum of k and t is 1 or greater; and the fluorine-containing alkene is a compound represented by Formula (3-1): $R^5CY^3\text{=}CY^4Y^5$ wherein $R^5$ is a hydrogen atom, a $C_{1-3}$ alkyl group, or a $C_{1-3}$ fluoroalkyl group; $Y^3$, $Y^4$ and $Y^5$ may be the same or different and each represents a hydrogen atom or a fluorine atom; with the proviso that when $R^5$ is not a fluoroalkyl group, at least one of $Y^3$ and $Y^4$ is a fluorine atom.

The production method of the present invention is explained in detail below.

Starting Material Compound

In the present invention, at least one fluorine-containing compound selected from the group consisting of chlorine-containing fluoroalkanes and fluorine-containing alkenes is used as a starting material.

The chlorine-containing fluoroalkanes are not particularly limited and examples thereof include a compound represented by Formula (1):

$$R^1\text{—}CCl_{2-(n+m)}H_nF_m\text{—}CCl_{2-(o+p)}H_oF_p\text{—}CCl_{3-(q+r)}H_qF_r$$

wherein $R^1$ is a $C_{1-4}$ alkyl group, a hydrogen atom, a fluorine atom, or a $C_{1-4}$ fluoroalkyl group that may contain a chlorine atom(s); n, m, o and p are each individually an integer of 0 to 2; q and r are each individually an integer of 0 to 3, with the proviso that n+m≤2, o+p≤2, q+r≤3, and n+m+o+p+q+r≤6; provided that when $R^1$ is neither a fluoroalkyl group nor a fluorine atom, the sum of m, p and r is 1 or greater; and a compound represented by Formula (2):

$$CCl_{3-(a+b)}H_aF_b\text{—}CCl_{3-(c+d)}H_cF_d$$

wherein a, b, c and d are each individually an integer of 0 to 3, a+b≤3, c+d≤3, b+d≥1, and a+b+c+d≤5.

Among the groups represented by $R^1$ in Formula (1), fluoroalkyl groups that may contain a chlorine atom(s) include linear or branched fluoroalkyl groups having about 1 to 4 carbon atoms that may contain up to 8 chlorine atoms. Specific examples of the fluoroalkyl groups include a perfluoroalkyl group and a fluoroalkyl group that contains 1 to 8 fluorine atoms. Among the groups represented by $R^1$, examples of alkyl groups include a methyl group, an ethyl group, an n-propyl group, an isopropyl group, an n-butyl group, a sec-butyl group, a tert-butyl group and like linear or branched alkyl groups.

Among the chlorine-containing fluoroalkanes represented by the above formula, a preferable compound is as shown below.

$$R^2\text{—}CCl_{2-(j+k)}H_jF_k\text{—}CCl_{3-(l+t)}H_lF_t \quad \text{Formula (1-1)}$$

wherein $R^2$ is a $C_{1-3}$ alkyl group, a hydrogen atom, a fluorine atom, or a $C_{1-3}$ fluoroalkyl group that may contain a chlorine atom(s); j and k are each individually an integer of 0 to 2; l and t are individually an integer of 0 to 3; j+k≤2; l+t≤3; and j+k+l+t≤4; with the proviso that when $R^2$ is neither a fluoroalkyl group nor a fluorine atom, the sum of k and t is 1 or greater.

Examples of $C_{1-3}$ alkyl groups represented by $R^2$ in Formula (1-1) include a methyl group, an ethyl group, a propyl group, an isopropyl group and the like. Examples of $C_{1-3}$ fluoroalkyl groups that may contain a chlorine atom(s) include the aforementioned alkyl groups having 1 to 7 fluorine atoms and 0 to 2 chlorine atoms substituted thereon.

Examples of chlorine-containing fluoroalkanes represented by Formula (1-1) include $CH_3CF_2CH_2Cl$, $CH_3CH_2CF_2CH_2Cl$, $CF_3CH_2Cl$, $CF_3CHClCH_2F$, $CF_2ClCH_2CFClCF_3$, $CH_3CFClCH_3$, $CF_3CH_2CHClCCl_2F$, $CH_3CHFCFHCl$, $CF_3CHClCHFCF_2Cl$, $CClHFCH_2F$ and the like.

An example of a fluorine-containing alkene includes a compound represented by the following formula:

$$R^3Y^1C\text{=}CY^2R^4 \quad \text{Formula (3)}$$

wherein $R^3$ and $R^4$ may be the same or different and each represents a $C_{1-4}$ alkyl group, a hydrogen atom, a fluorine atom, a chlorine atom, or a $C_{1-4}$ fluoroalkyl group that may contain a chlorine atom(s); be the same or different and each $Y^1$ and $Y^2$ may represents a hydrogen atom, a fluorine atom, or a chlorine atom; with the proviso that when $R^3$ and $R^4$ are neither a fluoroalkyl group nor a fluorine atom, at least one of $Y^1$ and $Y^2$ is a fluorine atom.

In Formula (3), examples of fluoroalkyl groups and alkyl groups represented by $R^3$ and $R^4$ include the same groups as those represented by $R^1$. Among the compounds represented by Formula (3), a compound shown below is preferable.

$$R^5CY^3\text{=}CY^4Y^5 \quad \text{Formula (3-1)}$$

wherein $R^5$ is a hydrogen atom, a $C_{1-3}$ alkyl group, or a $C_{1-3}$ fluoroalkyl group; $Y^3$, $Y^4$ and $Y^5$ may be the same or different and each represents a hydrogen atom or a fluorine atom; with the proviso that when $R^5$ is not a fluoroalkyl group, at least one of $Y^3$ and $Y^4$ is a fluorine atom. Examples of alkyl groups and fluoroalkyl groups represented by $R^5$ in Formula (3-1) are the same as those represented by $R^2$.

Specific examples of fluorine-containing alkenes represented by Formula (3-1) include the compounds represented by chemical formulae $CF_3CF\text{=}CF_2$, $CF_3CH\text{=}CFH$, $CH_3CF_2CF\text{=}CH_2$ and the like.

Catalyst

In the present invention, the catalyst is not particularly limited and any catalysts can be used as long as they are active in an addition reaction of hydrogen gas to an alkene compound or a hydrogen substitution reaction of a chlorine-containing compound with hydrogen gas. It is particularly preferable to use a catalyst comprising a noble metal component supported on a carrier.

Examples of the noble metals usable as catalytic components include Pd, Pt, Ru and Rh. Examples of carriers include activated carbon, porous alumina silicate represented by zeolite, aluminum oxide, silicon oxide, titanium oxide, zirconium oxide, zinc oxide, aluminum fluoride, a mixture of one or more of these carrier components, a composite of one or more of these carrier components, which are structurally combined, and the like.

The amount of noble metal supported on the carrier is not limited, and, for example, preferably the amount of the noble metal supported is about 0.001 to 50% by weight, more preferably about 0.001 to 20% by weight, and particularly preferably 0.01 to 10% by weight, based on the total weight of the catalyst supporting noble metal.

The method for preparing the catalyst is not particularly limited. An example of the method for preparing a catalyst comprising a noble metal component supported on a carrier is as below. That is, activated carbon or a like carrier is immersed in a solution containing a metal salt to impregnate the carrier with the solution, if necessary, followed by neutralization, sintering or a like operation, thereby obtaining the catalyst comprising a noble metal component supported on a carrier. The amount of the noble metal supported can be suitably controlled by adjusting the impregnation method, such as the concentration of the metal salt in the metal salt solution, the impregnation time, and the like.

Method for Producing Fluorine-Containing Alkane

The method of the present invention is to produce fluorine-containing alkane using at least one fluorine-containing compound selected from the group consisting of the aforementioned chlorine-containing fluoroalkanes and fluorine-containing alkenes as starting materials and reacting the starting materials with hydrogen gas in the presence of a catalyst.

Among the chlorine-containing fluoroalkanes, when a chlorine-containing fluoroalkane represented by Formula (1): $R^1—CCl_{2-(n+m)}H_nF_m—CCl_{2-(o+p)}H_oF_p—CCl_{3-(q+r)}H_qF_r$ (wherein $R^1$, n, m, o, p, q and r are the same as above) is used as a starting material, a fluorine-containing alkane represented by Formula: $R^1—CH_{2-m}F_m—CH_{2-p}F_p—CH_{3-r}F_r$ (wherein $R^1$, m, p and r are the same as above) can be produced by a substitution reaction of hydrogen for a chlorine atom(s). When a chlorine-containing fluoroalkane represented by Formula (2): $CCl_{3-(a+b)}H_aF_b—CCl_{3-(c+d)}H_cF_d$ (wherein a, b, c and d are the same as above) is used as a starting material, a fluorine-containing alkane represented by Formula: $CH_{3-b}F_b—CH_{3-d}F_d$ (wherein b and d are the same as above) can also be produced by the substitution reaction of hydrogen for a chlorine atom(s). For example, when a compound represented by Formula (1-1): $R^2—CCl_{2-(j+k)}H_jF_k—CCl_{3-(l+t)}H_lF_t$ (wherein $R^2$, j, k, l and t are the same as above) is used as a starting material, a fluorine-containing alkane represented by Formula: $R^2—CH_{2-k}F_k—CH_{3-t}F_t$ (wherein $R^2$, k and t are the same as above) can be produced by a hydrogen substitution reaction.

Among fluorine-containing alkenes, when a fluorine-containing alkene represented by Formula (3): $R^3Y^1C=CY^2R^4$ (wherein $R^3$, $R^4$, $Y^1$ and $Y^2$ are the same as above) is used as a starting material, a fluorine-containing alkane represented by Formula: $R^3Y^1CH—CHY^2R^4$ (wherein $R^3$, $R^4$, $Y^1$ and $Y^2$ are the same as above) can be produced by an addition reaction of hydrogen gas. For example, when a fluorine-containing alkene represented by Formula (3-1): $R^5CY^3=CY^4Y^5$ (wherein $R^5$, $Y^3$, $Y^4$ and $Y^5$ are the same as above) is used as a starting material, a fluorine-containing alkane represented by Formula: $R^5CHY^3—CHY^4Y^5$ (wherein $R^5$, $Y^3$, $Y^4$ and $Y^5$ are the same as above) can be produced.

In the method for producing fluorine-containing alkane of the present invention, the use of a plurality of catalysts having different catalytic activities is required. In this method, it is necessary to conduct a multistep reaction by contacting hydrogen gas and at least one fluorine-containing compound selected from the group consisting of chlorine-containing fluoroalkanes and fluorine-containing alkenes with a catalyst having the lowest activity in the first stage of the reaction, followed by contact thereof with a catalyst(s) in the order of lower to higher catalytic activity. By employing a multistep reaction method as described above, wherein a plurality of catalysts having different catalytic activities are used and the starting materials are contacted with a catalyst in the order of lower to higher catalytic activity, the temperature rise during the reaction can be suppressed without deteriorating the conversion rate, selectivity, and the like. This makes it possible to increase the amount of starting material supplied and to greatly improve the production efficiency of the target fluorine-containing alkane.

The catalytic activity of the catalyst varies depending on the types of catalyst metal and carrier used, and the amount of the catalyst metal supported. When identical catalyst metals and carriers are used, although there is an upper limit, there is a tendency for the catalytic activity to rise as the amount of the catalyst metal supported increases. Therefore, when catalysts comprising identical noble metal components are supported on identical carriers in different amounts, the fluorine-containing compound and hydrogen gas, which are starting materials, should be sequentially contacted with a catalyst comprising a smaller amount of noble metal component supported followed by a catalyst comprising a larger amount of noble metal component supported.

A catalyst can be made into one that has a lower catalytic activity by mixing it with an inactive substance to dilute it. An example of such an inactive substance is activated carbon, but is not limited thereto. When catalysts comprising different types of catalyst metal and/or carrier are used, by performing a preliminary experiment using the same starting material as that actually used, the intensity of the catalytic activity can be easily determined.

When a plurality of catalysts having different catalytic activities are used, the proportion of catalysts is not particularly limited and can be suitably selected, depending on the level of activity of the catalyst used, so as to suppress the heating during reaction, to prevent an excessive temperature rise, and to maintain the desirable conversion rate of the starting material and selectivity of the target product, as long as it meets the requirement that the fluorine-containing compound and hydrogen gas, which are starting materials, are made to contact with a catalyst having a smaller catalytic activity sequentially followed by that having a higher catalytic activity. For example, the proportion of the catalyst used may be such that, relative to 100 parts by weight of the catalyst having the highest activity, the total amount of other catalysts is about 50 to 400 parts by weight, and preferably about 70 to 300 parts by weight.

The structure of the reaction apparatus is not particularly limited. As an example of a usable reaction apparatus, two or more gas phase reactors are connected in series, wherein a catalyst having the lowest catalytic activity is placed in the first reactor of the reaction apparatus, and catalysts having sequentially higher catalytic activities are placed in the second and following reactors sequentially. Furthermore, it is also possible to use a single gas phase reactor, rather than a plurality of reactors, wherein a catalyst having the lowest catalytic activity is placed near the entrance and a catalyst having the highest catalytic activity is placed near the exit, so that the catalytic activities of the catalysts are sequentially arranged from low to high in the direction along which the starting material gas flows.

An example of each reactor usable in the reaction apparatus described above includes a tubular flow reactor. Examples of flow reactors include adiabatic reactors, multitubular reactors that are cooled using a heat transmittance medium. Preferably, the reactor is made of a material that is resistant to the corrosive action of hydrogen fluoride, such as Hastelloy, Inconel, Monel, or the like.

Because the production method of the present invention allows heating to be suppressed during the reaction, the target fluorine-containing alkane can be produced at a high production efficiency without actively performing cooling. Fluorine-containing alkane can be efficiently produced by, for example, a reaction apparatus with a simple structure such as only having cooling fins, without having to introduce a diluent into the reaction mixture as a coolant or use a complicated reaction apparatus provided with a jacket or an internal cooling coil.

The reaction temperature is not particularly limited but it must be set lower than the ignition point of hydrogen. The reaction temperature is generally about 50 to 400° C., preferably about 50 to 390° C., and more preferably about 50 to 380° C. The production method of the present invention can suppress heating during the reaction; therefore, compared to conventional methods, even in the case where the amount of starting material introduced is increased, the reaction temperature can be controlled within the above mentioned range. This allows the target fluorine-containing alkane to be produced at a high production efficiency.

The pressure during the reaction is not particularly limited and the reaction may be performed under reduced pressure, ordinary pressure, or the application of pressure. Usually, the reaction may be performed under a level of pressure that is close to atmospheric pressure (0.1 MPa).

The amount of hydrogen gas used is preferably about 1 to 10 mol, preferably about 1 to 8 mol, and more preferably about 1 to 5 mol per mole of the starting material, i.e., at least one fluorine-containing compound selected from the group consisting of chlorine-containing fluoroalkanes and fluorine-containing alkenes.

The reaction time is not particularly limited and, when a chlorine-containing fluoroalkane is used as the starting material, it is preferable that the reaction time be selected in such a manner that the contact time represented by W/Fo, i.e., the ratio of the total weight of the catalyst used in all stages of the reaction W (g) relative to the total flow rate Fo (the flow rate: cc/sec at 0° C. and 0.1 MPa) of the starting material gases (i.e., the total amount of the fluorine-containing compound and hydrogen gas) that are supplied to the reaction apparatus, is generally about 0.5 to 60 g·sec/cc, more preferably about 1 to 50 g·sec/cc, and still more preferably about 1 to 40 g·sec/cc. Furthermore, when fluorine-containing alkene is used as the starting material, the contact time represented by W/Fo is preferably about 0.5 to 30 g·sec/cc, more preferably about 0.5 to 20 g·sec/cc, and still more preferably about 0.5 to 15 g·sec/cc.

Advantageous Effects of Invention

In terms of the method for producing fluorine-containing alkane wherein chlorine-containing fluoroalkane or fluorine-containing alkene is used as a starting material and reacted with hydrogen gas, the present invention provides a method that can suppress the temperature rise during the reaction without decreasing the conversion rate and selectivity; therefore, it can significantly improve the production efficiency by increasing the introduction rate of the starting material.

DESCRIPTION OF EMBODIMENTS

The present invention is explained in further detail below with reference to the Examples.

Example 1

Using a reaction tube made of SUS having an inside diameter of 50 mm and a length of 128 cm, 530 g of a catalyst containing Pd supported on activated carbon (the amount of Pd supported: 0.1% by weight (the total amount of the carrier and Pd is defined as 100% by weight) (0.1 wt % Pd/C catalyst) was placed in the area within the range of about 10 to 70 cm from the entrance of the reaction tube and 530 g of a catalyst containing Pd supported on activated carbon (the amount of Pd supported: 0.25% by weight) (0.25 wt % Pd/C catalyst) was placed in the area within the range of about 70 to 120 cm from the entrance. The catalysts were dried at 150° C. and reduced by flowing hydrogen at 200° C. beforehand.

After heating the reaction tube described above to about 260° C. using a heater, $CF_3CF_2CH_2Cl$ (HCHC-235cb) and hydrogen were supplied therein at a rate of 945 ml/min (the flow rate at 0° C. and 0.1 MPa, the same applies to the following) and 1,920 ml/min respectively.

The exit gas from the reactor was analyzed by gas chromatography, with the result that the conversion of $CF_3CF_2CH_2Cl$ (HCFC-235cb) was 94.5% and the selectivity of $CF_3CF_2CH_3$ (HFC-245cb) was 96.9%. The maximum temperature inside the reactor was 336° C.

This method obtained the target product, i.e., $CF_3CF_2CH_3$ (HFC-245cb), at a rate of 865 ml/min (0.82 ml/min/g-cat).

Comparative Example 1

1,059 g of catalyst containing Pd supported on activated carbon (the amount of Pd: 0.25% by weight) (0.25 wt % Pd/C catalyst) was placed in a reaction tube made of SUS having an inside diameter of 50 mm and a length of 128 cm. The catalyst was dried at 150° C. and reduced by flowing hydrogen at 200° C. beforehand.

After heating the reaction tube described above to about 260° C. using a heater, $CF_3CF_2CH_2Cl$ (HCFC-235cb) and hydrogen were supplied therein at a flow rate of 702 ml/min and 1,991 ml/min respectively.

The exit gas from the reactor was analyzed by gas chromatography, with the result that the conversion of $CF_3CF_2CH_2Cl$ (HCFC-235cb) was 95.5% and the selectivity of $CF_3CF_2CH_3$ (HFC-245cb) was 96.7%. The maximum temperature inside the reactor was 381° C.

This method obtained the target product, i.e., $CF_3CF_2CH_3$ (HFC-245cb), at a rate of 648 ml/min (0.61 ml/min/g-cat).

In Example 1 and Comparative Example 1, almost the same amounts of catalysts were used. However, in Example 1, the half amount thereof was a catalyst having low catalytic activity. Comparing the results of Example 1 to those of Comparative Example 1, the conversion rate of the starting material and the selectivity of fluorine-containing alkane were almost the same; however, the temperature rise in the reactor was suppressed in Example 1 compared to Comparative Example 1. As a result, in contrast to Comparative Example 1 wherein the introduction amount of the starting material could not be increased, the introduction amount of the starting material in Example 1 could be increased, enhancing the production amount of the target product, i.e., $CF_3CF_2CH_3$ (HFC-245eb) per unit time.

Example 2

Using a reaction tube made of SUS having an inside diameter of 25 mm and a length of 140 cm, 100 g of a catalyst containing Pd supported on activated carbon (the amount of Pd supported: 0.2% by weight) (0.2 wt % Pd/C catalyst) was placed in the area within the range of about 10 to 50 cm from the entrance of the reaction tube, 100 g of catalyst containing Pd supported on activated carbon (the amount of Pd supported: 0.3% by weight) (0.3 wt % Pd/C catalyst) was placed in the area within the range of about 50 to 90 cm from the entrance of the reaction tube, and 100 g of catalyst containing Pd supported on activated carbon (the amount of Pd supported: 0.6% by weight) (0.6 wt % Pd/C catalyst) was placed in the area within the range of about 90 to 130 cm from the entrance of the reaction tube. The catalysts were dried at 150° C. and reduced by flowing hydrogen at 200° C. beforehand.

From the entrance of the reaction tube where the 0.2 wt % Pd/C catalyst was placed, hexafluoropropene ($CF_3CF=CF_2$) and hydrogen were flowed into the reaction apparatus described above at flow rates of 1,597 ml/min and 2,256 ml/min respectively. The internal temperature of the reaction tube when the hydrogen and hexafluoropropene were introduced was 25° C.

The exit gas from the reactor was analyzed by gas chromatography, with the result that the conversion of hexafluoropropene was 98.9% and the selectivity of $CF_3CHFCHF_2$ (HFC-236ea) was 100%. The maximum temperature inside the reactor was 268° C.

This method made it possible to obtain the target product, i.e., $CF_3CHFCHF_2$ (HFC-236ea), at a rate of 1,578 ml/min (5.26 ml/min/g-cat).

Comparative Example 2

270 g of catalyst containing Pd supported on activated carbon (the amount of Pd supported: 3% by weight) (3 wt % Pd/C catalyst) was placed in a reaction tube made of SUS having an inside diameter of 25 mm and a length of 120 cm, followed by ice-cooling. The catalyst was dried at 150° C. and reduced by flowing hydrogen at 200° C. beforehand.

Into the reaction tube described above, hexafluoropropene and hydrogen were supplied at flow rates of 769 ml/min and 1,662 ml/min respectively. The internal temperature of the reaction tube when the hydrogen and hexafluoropropene were introduced was 0° C.

The exit gas from the reactor was analyzed by gas chromatography, with the result that the conversion of hexafluoropropene was 100% and the selectivity of $CF_3CHFCHF_2$ (HFC-236ea) was 99.6%. The maximum temperature inside the reactor was 293° C.

This method made it possible to obtain the target product, i.e., $CF_3CHFCHF_2$ (HFC-236ea), at a rate of 764 ml/min (2.83 ml/min/g-cat).

In Example 2 and Comparative Example 2 described above, reaction apparatuses having almost the same size were used and the amounts of catalyst used were also almost the same. The difference lies in that three types of catalysts having different activities were used in Example 2 but a single catalyst having high activity was used in Comparative Example 2.

Comparing the results of Example 2 to those of Comparative Example 2, the conversion rate and selectivity were almost the same level. However, in Comparative Example 2, regardless of the use of an ice-cooled reaction tube, the temperature significantly rose during the reaction; therefore, the introduction amount of the starting material could not be increased. In contrast, although no ice-cooling or like active cooling was performed, the temperature rise in the reaction tube was suppressed in Example 2. This allowed the introduction amount of the starting material to be increased, enhancing the production amount of the target product, i.e., $CF_3CHFCHF_2$ (HFC-236ea) per unit of time.

Example 3

Using a reaction tube made of SUS having an inside diameter of 25 mm and a length of 140 cm, 100 g of catalyst containing Pd supported on activated carbon (the amount of Pd supported: 0.2% by weight) (0.2 wt % Pd/C catalyst) was placed in the area within the range of about 10 to 50 cm from the entrance of the reaction tube, 100 g of catalyst containing Pd supported on activated carbon (the amount of Pd supported: 0.3% by weight) (0.3 wt % Pd/C catalyst) was placed in the area within the range of about 50 to 90 cm from the entrance of the reaction tube, and 100 g of catalyst containing Pd supported on activated carbon (the amount of Pd supported: 0.6% by weight) (0.6 wt % Pd/C catalyst) was placed in the area within the range of about 90 to 130 cm from the entrance of the reaction tube. The catalysts were dried at 150° C. and reduced by flowing hydrogen at 200° C. beforehand.

The reaction tube described above was heated to 150° C. using a heater, and $CF_3CF=CHF$ (HFC-1225ye) and hydrogen were flowed at 1,032 ml/min and 2,515 ml/min respectively from the entrance of the reaction tube where 0.2 wt % Pd/C catalyst was placed. The internal temperature of the reaction tube was 150° C. when the hydrogen and pentafluoropropene were introduced.

The exit gas from the reactor was analyzed by gas chromatography, with the result that the conversion of $CF_3CF=CHF$ (HFC-1225ye) was 98.0% and the selectivity of $CF_3CHFCH_2F$ (HFC-245eb) was 99.4%. The maximum temperature inside the reactor was 292° C.

This method made it possible to obtain the target product, i.e., $CF_3CHFCH_2F$ (HFC-245eb), at a rate of 1,005 ml/min.

Comparative Example 3

38 g of catalyst containing Pd supported on activated carbon (the amount of Pd supported: 3% by weight) (3 wt % Pd/C catalyst) was placed in a reaction tube made of SUS having an inside diameter of 20 mm and a length of 68 cm. The catalyst was dried at 150° C. and reduced by flowing hydrogen at 200° C. beforehand.

Into the reaction tube described above, $CF_3CF=CHF$ (HFC-1225ye) and hydrogen were flowed at flow rates of 267 ml/min and 1,065 ml/min respectively. The internal temperature of the reaction tube when hydrogen and pentafluoropropene were introduced was 25° C.

The exit gas from the reactor was analyzed by gas chromatography, with the result that the conversion of $CF_3CF=CHF$ (HFC-1225ye) was 99.5% and the selectivity of $CF_3CHFCH_2F$ (HFC-245eb) was 98.9%. The maximum temperature inside the reactor was 245° C.

This method made it possible to obtain the target product, i.e., $CF_3CHFCH_2F$ (HFC-245eb), at a rate of 262 ml/min.

In Example 3 and Comparative Example 3 described above, reaction apparatuses with different sizes were used. Due to the large amount of heat generated, a larger reaction apparatus could not be used in Comparative Example 3. As to the catalyst, three types of catalysts having different catalytic activities were used in Example 3, but a single catalyst having high activity was used in Comparative Example 3. As a result, because a large amount of heat was generated by the reaction, the amount of catalyst used was limited in Comparative Example 3.

Comparing the results of Example 3 to those of Comparative Example 3, they are similar in the conversion rate and selectivity, but due to the heat generated, the introduction amount of the starting material could not be increased in Comparative Example 3. In contrast, in Example 3, the temperature rise in the reaction tube was suppressed; therefore, the production amount of $CF_3CHFCHF_2$ (236ea) per unit of time was increased.

The invention claimed is:

1. A method for producing fluorine-containing alkane comprising reacting at least one chlorine-containing fluoroalkane with hydrogen gas in the presence of catalysts having different catalytic activities,
   wherein the catalysts having different catalytic activities are:
   those containing Pd supported on activated carbon with different supporting amounts; or
   those made by mixing Pd supported on activated carbon with an activated carbon to dilute it in different dilution rates, and
   wherein the at least one chlorine-containing fluoroalkane and hydrogen gas, which are starting materials, are sequentially contacted with a catalyst containing a smaller amount of Pd to a catalyst containing a larger amount of Pd.

2. The method according to claim 1, wherein the reaction proceeds in a reaction apparatus in which two or more reaction tubes charged with catalysts having different catalytic activities are connected in series.

3. The method according to claim 1, wherein the chlorine-containing fluoroalkane is at least one member selected from the group consisting of:
   a compound represented by Formula (1):

$$R^1-CCl_{2-(n+m)}H_nF_m-CCl_{2-(o+p)}H_oF_p-CCl_{3-(q+r)}H_qF_r$$

wherein $R^1$ is a $C_{1-4}$ alkyl group, a hydrogen atom, a fluorine atom, or a $C_{1-4}$ fluoroalkyl group that may contain a chlorine atom(s); n, m, o and p are each individually an integer of 0 to 2; q and r are each individually an integer of 0 to 3, with the proviso that $n+m \le 2$, $o+p \le 2$, $q+r \le 3$, and $n+m+o+p+q+r \le 6$; provided that when $R^1$ is neither a fluoroalkyl group nor a fluorine atom, the sum of m, p and r is 1 or greater; and
   a compound represented by Formula (2):

$$CCl_{3-(a+b)}H_aF_b-CCl_{3-(c+d)}H_cF_d$$

wherein a, b, c and d are each individually an integer of 0 to 3, $a+b \le 3$, $c+d \le 3$, $b+d \ge 1$, and $a+b+c+d \le 5$.

4. The method according to claim 1, wherein the chlorine-containing fluoroalkane is a compound represented by Formula (1-1):

$$R^2-CCl_{2-(j+k)}H_jF_k-CCl_{3-(l+t)}H_lF_t$$

wherein $R^2$ is a $C_{1-3}$ alkyl group, a hydrogen atom, or a fluorine atom, or a $C_{1-3}$ fluoroalkyl group that may contain a chlorine atom(s); j and k are each individually an integer of 0 to 2; l and t are each individually an integer of 0 to 3; $j+k \le 2$; $l+t \le 3$; and $j+k+l+t \le 4$; with the proviso that when $R^2$ is neither a fluoroalkyl group nor a fluorine atom, the sum of k and t is 1 or greater.

* * * * *